(12) United States Patent
Choi

(10) Patent No.: US 10,160,589 B2
(45) Date of Patent: Dec. 25, 2018

(54) BIOSENSOR STRIP DISPENSING APPARATUS AND STRIP CARTRIDGE USED BY BEING COUPLED THERETO

(71) Applicant: In Sang Choi, Anyang-si (KR)

(72) Inventor: In Sang Choi, Anyang-si (KR)

( * ) Notice: Subject to any disclaimer, the term of this patent is extended or adjusted under 35 U.S.C. 154(b) by 0 days.

(21) Appl. No.: 15/324,072

(22) PCT Filed: Jul. 6, 2015

(86) PCT No.: PCT/KR2015/006958
§ 371 (c)(1),
(2) Date: Jan. 5, 2017

(87) PCT Pub. No.: WO2016/006897
PCT Pub. Date: Jan. 14, 2016

(65) Prior Publication Data
US 2017/0158415 A1   Jun. 8, 2017

(30) Foreign Application Priority Data

Jul. 7, 2014   (KR) .................. 10-2014-0084707
Jul. 7, 2014   (KR) .................. 10-2014-0084708

(51) Int. Cl.
*B65D 83/08* (2006.01)
*B65H 3/24* (2006.01)
(Continued)

(52) U.S. Cl.
CPC ..... *B65D 83/0817* (2013.01); *B65D 83/0829* (2013.01); *B65H 1/12* (2013.01);
(Continued)

(58) Field of Classification Search
CPC .. B65D 83/0817; B65D 83/0829; B65H 1/12; B65H 3/24; B65H 2402/41; B65H 2403/41
(Continued)

(56) References Cited

U.S. PATENT DOCUMENTS 9,011,793 B2 *  4/2015  Choi ................ A61B 5/14532
                                                      422/404
2007/0241134 A1 * 10/2007 Gurrisi ............... B65D 83/384
                                                      222/153.11
(Continued)

FOREIGN PATENT DOCUMENTS

JP    2010094402    *  4/2010  ............. A61B 5/157
JP    2010094402 A  *  4/2010  ............. A61B 5/157
(Continued)

OTHER PUBLICATIONS

PCT International Search Report, PCT/KR2015/006958, dated Sep. 23, 2015.

*Primary Examiner* — Rakesh Kumar
(74) *Attorney, Agent, or Firm* — Yakov S. Sidorin; Quarles & Brady LLP

(57) ABSTRACT

Disclosed are a biosensor strip dispensing apparatus and a strip cartridge used by being coupled thereto. The present invention enables opening of a dispensing hole and dispensing of a strip to be performed simultaneously by an open plate and a dispensing plate which move by being interlocked with each other, and thus the present invention can form a biosensor strip dispensing apparatus which enables a strip to be easily dispensed when using the strip, has a great strip protection effect due to sealing of the inner part of a body, and has a compact size. In addition, the present invention enables a strip to be upwardly pressed by an up-and-down elastic unit, while adjusting the elastic force upwardly applied by a friction elastic unit so that the amount of change in a frictional force applied between the uppermost strip and a protrusion is reduced, and thus, the present invention can form a strip cartridge by which a strip is easily dispensed.

9 Claims, 12 Drawing Sheets

(51) Int. Cl.
    B65H 1/12      (2006.01)
    G01N 27/26     (2006.01)
    G01N 33/50     (2006.01)
    G01N 33/66     (2006.01)
    C12Q 1/00      (2006.01)
    G01N 27/327    (2006.01)
    B65H 1/26      (2006.01)

(52) U.S. Cl.
    CPC .............. B65H 1/266 (2013.01); B65H 3/24 (2013.01); C12Q 1/006 (2013.01); G01N 27/26 (2013.01); G01N 27/3272 (2013.01); G01N 33/50 (2013.01); G01N 33/66 (2013.01); B65H 2402/41 (2013.01); B65H 2403/41 (2013.01)

(58) Field of Classification Search
    USPC ........................................................ 221/250
    See application file for complete search history.

(56) References Cited

U.S. PATENT DOCUMENTS

| | | | | |
|---|---|---|---|---|
| 2008/0064278 A1* | 3/2008 | Oaroche | ................ | A47K 10/16 442/59 |
| 2009/0270765 A1* | 10/2009 | Ghesquiere | ........ | A61B 5/14532 600/583 |
| 2011/0272430 A1* | 11/2011 | Muderlak | ............. | E05B 1/0069 221/197 |
| 2011/0313267 A1* | 12/2011 | Choi | .................. | A61B 5/14532 600/365 |
| 2014/0123735 A1* | 5/2014 | Uenosono | ........ | G01N 33/48785 73/61.41 |
| 2014/0312054 A1* | 10/2014 | Crawford | ........... | B65D 83/0418 221/232 |
| 2017/0158415 A1* | 6/2017 | Choi | ........................ | B65H 1/12 |

FOREIGN PATENT DOCUMENTS

| | | | | |
|---|---|---|---|---|
| JP | 2010094402 A | | 4/2010 | |
| KR | 1020100032413 A | | 3/2010 | |
| KR | 101101199 B1 | | 1/2012 | |
| KR | 1020130032461 A | | 4/2013 | |
| KR | 101348410 B1 * | | 1/2014 | ............. A61B 5/157 |
| KR | 101348410 B1 | | 1/2014 | |
| KR | 1020140042870 A | | 4/2014 | |
| WO | WO-2013018315 A1 * | | 2/2013 | ........ G01N 33/48785 |

* cited by examiner

[Fig. 13]
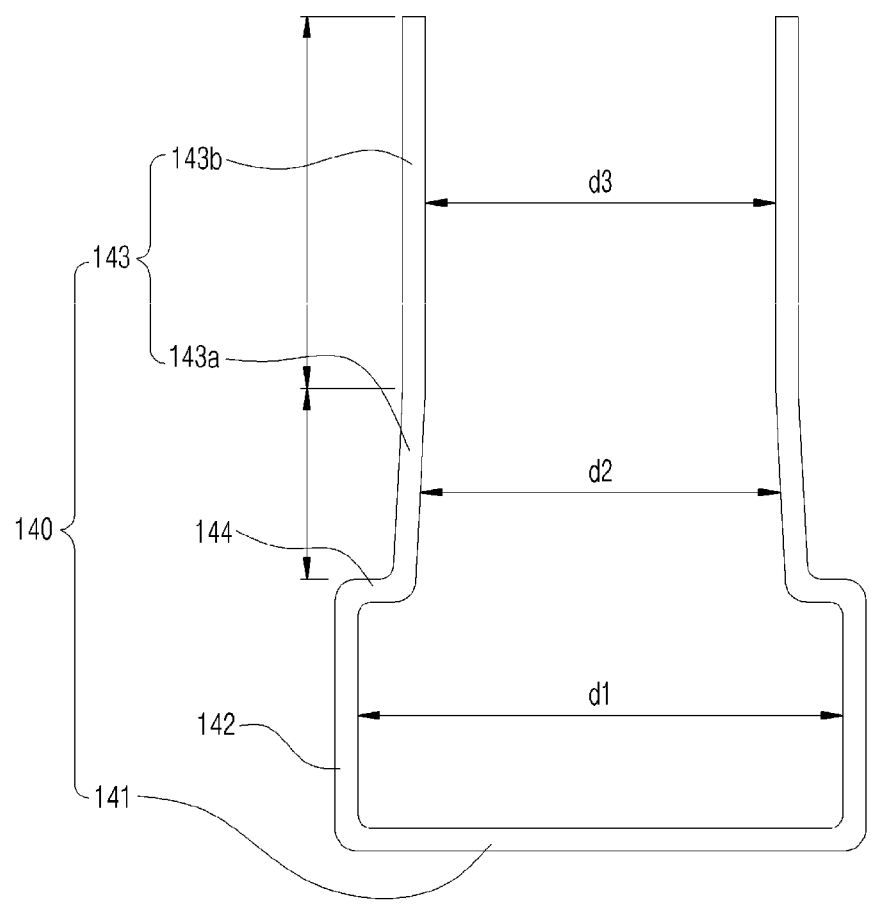

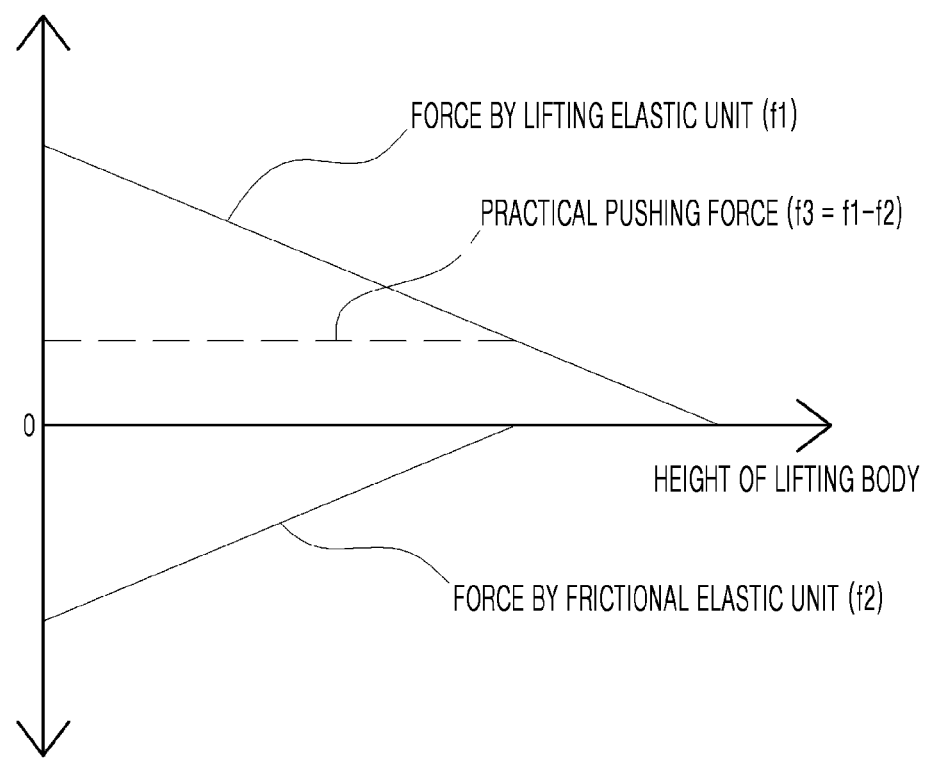
[Fig. 14]

BIOSENSOR STRIP DISPENSING APPARATUS AND STRIP CARTRIDGE USED BY BEING COUPLED THERETO

CROSS-REFERENCE TO RELATED APPLICATIONS

This application represents the national stage entry of PCT International Application No. PCT/KR2015/006958 filed Jul. 6, 2015 and claims priority to Korean Patent Application No. 10-2014-0084707 filed Jul. 7, 2014 and Korean Patent Application No. 10-2014-0084708 filed Jul. 7, 2014. The contents of the international application are hereby incorporated by reference as if set forth in their entirety herein.

TECHNICAL FIELD

The present disclosure relates to a biosensor strip dispensing apparatus and a strip cartridge used in a state of being coupled to the biosensor strip dispensing apparatus. More particularly, the present disclosure relates to a blood glucose measuring strip dispensing apparatus that is capable of storing and dispensing a biosensor strip used for analyzing a biological sample including blood, and relates to a strip cartridge used in the state of being coupled to the blood glucose measuring strip dispensing apparatus.

BACKGROUND ART

A biosensor refers to a miniaturized sensor that includes a certain biological object combined with a signal transducer, and converts information about the amount of a substance of interest among various mixtures into an electrical signal using a biological substance.

The biosensor may be used to generate an electrical signal that is proportional to the amount of any substance to be analyzed or a group of substances associated therewith. For example, the biosensor may be used as a blood sensor for detecting a blood glucose value from blood collected from the blood of a diabetic patient.

Such a biosensor may be implemented using a small-sized device such that the user can use the biosensor easily and quickly.

An electrochemical biosensor, which is a kind of biosensor, is configured to directly convert the amount of a biological material into an electrical analogue signal, and then to convert the electrical analogue signal into a digital signal, among various initial signal conversion principles.

For example, when galactose oxidase is fixed to a platinum electrode, the platinum electrode is immersed in a sample solution containing galactose, and then a voltage is applied to the platinum electrode, a chemical reaction occurs on the surface of the electrode. Hydrogen peroxide produced as a result of the chemical reaction is oxidized on the platinum electrode, and an amount of charge proportional to the oxidation amount is generated.

The amount of charge generated per unit time is proportional to the concentration of hydrogen peroxide generated around the platinum electrode by the galactose oxidase, so that the concentration of galactose can be determined by measuring the current flowing therearound. Besides the method of measuring the current, the same result can be obtained by measuring a pH change or measuring a reduced amount in oxygen concentration.

The electrochemical biosensor also includes a type of obtaining information concerning the concentration of a desired substance from the current value, and a type of performing the same operation from a potential difference and a resistance value.

For the measurement through a biosensor, it is necessary to use a measuring device. In connection with such a measuring device, Korean Patent Laid-Open Publication No. 10-2013-0032461 discloses "Biosensor and Measuring Device thereof." Specifically, the Korean Patent Laid-Open Publication discloses a measuring device that is formed with a receiving part into which a biosensor is inserted. A corresponding dedicated fastening portion is formed on each of the contact surfaces where the biosensor and the receiving part of the measuring device are in contact with each other, and the biosensor is configured to be capable of being inserted into the receiving portion only when the respective dedicated fastening portions are engaged with each other. With this arrangement, only the biosensor and the measuring device which are matched with each other can be coupled to each other so that reliable measuring results can be obtained.

Meanwhile, Korean Patent No. 10-1348410 discloses "Blood Glucose Measuring Strip Accommodating and Storage Device" as a device for storing and supplying a biosensor (strip). Specifically, the device includes: a housing that stores a plurality of strips arranged in a row to collect body fluid; an operating member that is opened at one side to allow the housing to be inserted into the operating member and rotates at a predetermined angle around a rotary shaft provided on an outer surface of the housing in order to discharge the strips; a first conveying member that is installed inside the housing in order to discharge the strips to the outside through a discharge port and converts the rotational motion of the operating member into an upward linear motion in order to convey the strips upward; and a second conveying member that is provided such that one side of the housing is opposite to the discharge port in order to convey an unused strip to a discharge region.

According to the strip accommodating device of Korean Patent No. 10-1348410, because one of a plurality of strips (biosensors) is automatically discharged through a discharge port, there are advantages in that the discharge time of the strip can be shortened, and the portability and operability of the product can be facilitated.

However, in a conventional general measuring device including the measuring device disclosed in Korean Patent Laid-Open No. 10-2013-0032461, it is necessary to confirm a measured value after the biosensor strip is inserted into the measuring device and to separate the biosensor strip from the measuring device. However, since the biosensor strips and the measuring device must be stored separately, and the biosensor strip must be replaced whenever a measurement is performed, there is a great inconvenience in use.

Also, as disclosed in Korean Patent Laid-Open Publication No. 10-2013-0032461 and Korean Patent No. 10-1348410, the conventional device includes a storage device of a strip (biosensor) and a blood glucose measuring device, which are generally separated from each other. The use of the devices is very complicated, which may become more inconvenient for an insulin-dependent patient who has to measure blood glucose several times a day.

In the strip storage device disclosed in Korean Patent Laid-Open Publication No. 10-2013-0032461, because the strips stacked by the elastic module and the guide unit are configured to be simply pressed, different frictional forces act on the stacked strips when the stacked strips are sequentially dispensed from the strip storage device so that there is a limit in smooth dispensing.

DETAILED DESCRIPTION OF THE INVENTION

Technical Problem

The present disclosure is to provide a biosensor strip dispensing apparatus that stores biosensors, in particular biosensor strips used for analyzing a biological sample including blood, and allows the biosensor strips to be automatically dispensed such that several measurements can be performed without replacing the biosensor strips.

In addition, the present disclosure is to provide a strip cartridge that stores biosensor strips to be dispensed, and is capable of minimizing a variation in frictional force acting on a strip that is being dispensed.

Technical Solution

In order to achieve the above described objects, there is provided a biosensor strip dispensing apparatus that may include: a body configured to accommodate at least one biosensor strip therein, and having a dispensing port formed in a front portion thereof to dispense the strip through the dispensing port; a sealing lever provided with a covering piece to shield the dispensing port, the covering piece configured to rotate about a first rotation shaft in an opening direction in which the covering piece opens the dispensing port and a shielding direction that is opposite to the opening direction; an opening plate connected to or supporting the sealing lever to rotate the sealing lever in the opening direction and the shielding direction while being slid back and forth on the body; and a dispensing plate interlocked with the opening plate to be slid in the same direction as the opening plate, the dispensing plate being configured to push the strip forward at a rear side of the strip.

Here, the biosensor strip dispensing apparatus may further include a first elastic unit made of an elastic body and configured to elastically support the sealing lever in the opening direction. The sealing lever may further include: a front arm extending forward from the first rotation shaft, and connected to the covering piece, which is bent downwardly, at a front end thereof; a rear arm extending rearward from the first rotation shaft; and an adjustment projection bent downwardly at a rear end of the rear arm. The opening plate may further include: a front end portion configured to support a lower end of the adjustment projection in a state where the covering piece shields the dispensing port; and a central portion extending rearward from the front end portion and formed to be lower than the front end portion, the central portion being configured to support the lower end of the adjustment projection in the state where the covering piece opens the dispensing port.

In addition, the opening plate may include an inclined portion that connects the front end portion and the central portion to each other and supports the lower end of the adjustment projection.

A plurality of the strips may be provided and may be stacked one on another within a cartridge. The body may include a storage hole formed to accommodate the cartridge. The biosensor strip dispensing apparatus may further include: a door rotatably coupled to the body to open/close the storage hole; and a second elastic unit made of an elastic body to elastically support the door in a direction where the door shields the storage hole.

The biosensor strip dispensing apparatus may further include a drive motor and a gear assembly connecting the drive motor to the opening plate and the dispensing plate.

At this time, the opening plate may be positioned outside the body, and the dispensing plate may be positioned inside the body. The gear assembly may include a first gear rotated by being connected to the opening plate and a second gear rotated by being connected to the dispensing plate.

The biosensor strip dispensing apparatus according to the present disclosure may further include: an abutment configured to support a lower surface of the strip when the strip is dispensed; and a contact terminal configured to support an upper surface of the strip when the strip is dispensed, and electrically connected to an electrode of the strip.

Here, the contact terminal may be coupled to the body to be rotatable about a third rotation shaft, and the biosensor strip dispensing apparatus may further include a third elastic unit made of an elastic body to elastically support the contact terminal in a direction where the contact terminal supports the strip.

The contact terminal may include a pushing surface formed to be inclined along the third rotation shaft, and the biosensor strip dispensing apparatus may further include a release button configured to move back and forth with respect to the pushing surface in a direction parallel to the third rotation shaft.

In the biosensor strip dispensing apparatus according to the present disclosure, a packing may be coupled to the covering piece to seal the dispensing port.

In order to achieve the above described objects, there is also provided a strip cartridge configured to store a plurality of biosensors to be dispensed outwardly. The strip cartridge may include: a housing including a stacking space in which the strips are vertically stacked, latching steps by which opposite side edges of an uppermost strip are caught, and a dispensing opening that is opened to allow the uppermost strip to be dispensed forward; a lifting body configured to vertically slid within the housing and to support a lower side of the strips; a lifting elastic unit made of an elastic body and configured to elastically support the lifting body upwardly; and a frictional elastic unit made of an elastic body and configured to rub against the lifting body.

The frictional elastic unit is configured such that, when the lifting body is located at a relatively lower position, the frictional elastic unit is deformed greatly to store a large elastic force, and when the lifting body is located at a relatively higher position, the frictional elastic unit is deformed less to store a small elastic force.

In addition, the frictional elastic unit may include: a lower end connection section; an elastic storage section extending upward from opposite ends of the lower end connection section and having a width larger than a width of the lifting body; a deformation section formed above the elastic storage section to at least partially rub against the lifting body, the deformation section including upper ends that are formed as free ends and having a width that is equal to or smaller than the width of the lifting body; and an intermediate connection section that connects the elastic storage section and the deformation section with each other.

Here, the deformation section may be configured to be divided into a lower deformation section having a width that decreases toward an upper side, and an upper deformation section extending upwardly from the upper side of the lower deformation section.

In addition, in the strip cartridge according to the present disclosure, the lifting body may include an insertion recess formed on a bottom surface of the lifting body and a portion of the lifting elastic unit may be inserted into the insertion recess.

The strip cartridge may further include a base plate coupled to a lower side of the housing to support the lifting elastic unit.

At this time, the frictional elastic unit may be formed in a form of a bent wire, and the base plate may include a support recess formed at a lower side thereof. A portion of the frictional elastic unit may be inserted into the support recess to be supported.

In addition, the housing may have a slit formed in a side wall thereof, and the frictional elastic unit may be inserted into the slit to be elastically deformed.

In addition, in the strip cartridge according to the present disclosure, the housing may include a partition formed to separate the housing into a dehumidifying space in which a dehumidifying agent is accommodated and the stacking space, and the stacking space and the dehumidifying space may be configured to communicate with each other through an upper end of the partition.

Advantageous Effects

According to the present disclosure, the opening of the dispensing port and the dispensing of a strip can be performed together by the opening plate and the dispensing plate, which move in cooperation with each other. Thus, it is possible to provide a compact biosensor strip dispensing apparatus that is excellent in strip protection effect according to the internal sealing of the body while easily dispensing strips when using the strips.

In addition, according to the present disclosure, the strips are adapted to be pressed upward by the lifting elastic unit and the elastic force applied upward is adapted to be adjusted by the frictional elastic unit. Thus, it is possible to reduce a variation in frictional force acting between the strip located at the uppermost position and latching steps, thereby facilitating the dispensing of the strip.

BRIEF DESCRIPTION OF THE DRAWINGS

FIG. 13 is a view illustrating a frictional elastic unit illustrated in FIG. 12 in a separated state; and FIG. 14 is a graph representing an elastic force generated by a lifting elastic unit and a frictional elastic unit as a lifting body is moved up within the housing.

DESCRIPTIONS OF REFERENCE NUMERALS OF DRAWINGS

Figure 1:
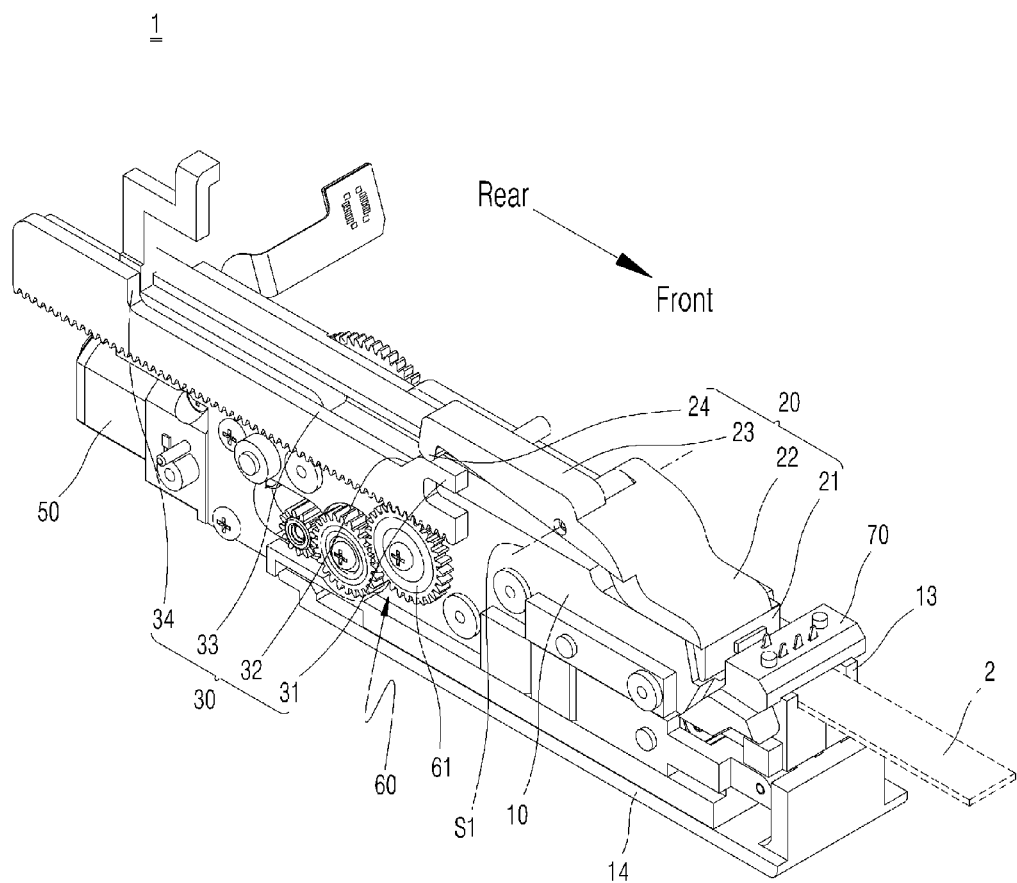
FIG. 1 is a perspective view illustrating a biosensor strip dispensing apparatus according to the present disclosure.

1: biosensor strip dispensing apparatus 2: strip 10: body 11: dispensing port 12: storage hole 13: abutment 14: door 15: inlet port 20: sealing lever 21: covering piece 22: front arm 23: rear arm 24: adjustment projection 30: opening plate 31: front end portion 32: inclined portion 33: central portion 34: stop portion 40: dispensing plate 41: pressing portion 42: supporting portion 50: drive motor 60: gear assembly 61: first gear 62: second gear 70: contact terminal 71: terminal 80: release button 100: strip cartridge 110: housing 111: stacking space 112: dehumidifying space 113: partition 114: latching step 115: dispensing opening 116: side wall 117: slit 118: coupling recess 120: lifting body 121: insertion recess 130: lifting elastic unit 140: frictional elastic unit 141: lower end connection section 142: elastic storage section 143: deformation section 143a: lower deformation section 143b: upper deformation section 144: intermediate connection section 150: base plate 151: coupling projection 152: supporting recess E1: first elastic unit E2: second elastic unit E3: third elastic unit S1: first rotation shaft S2: second rotation shaft S3: third rotation shaft

MODE FOR CARRYING OUT THE INVENTION

Hereinafter, exemplary embodiments of the present disclosure will be described in detail with reference to the accompanying drawings. In the description of the present disclosure, the description of the well-known function or structure will be omitted in order to clear the subject matter of the present disclosure.

Prior to describing a strip cartridge 100 according to the present disclosure, first descriptions will be made on a biosensor strip dispensing apparatus 1 that is used in a state where the strip cartridge 100 is coupled thereto.

Figure 2:
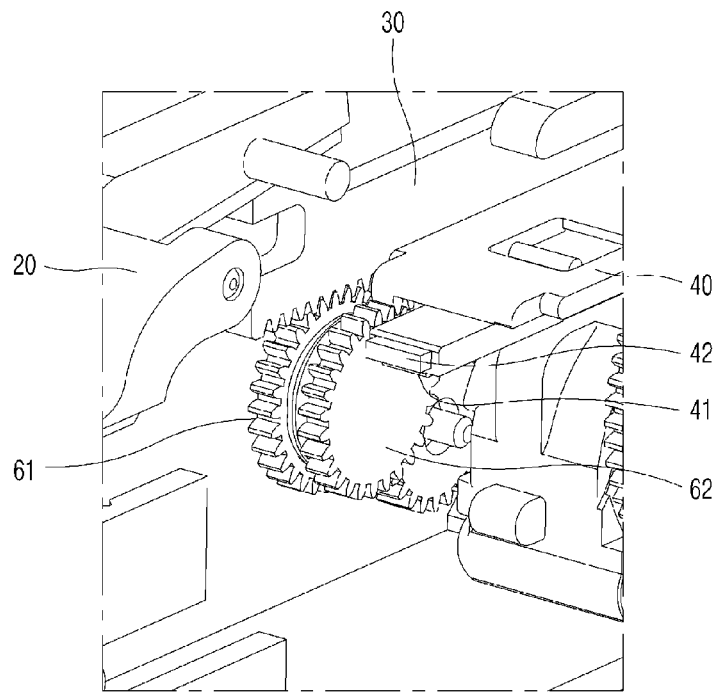
FIG. 2 is a perspective view illustrating the biosensor strip dispensing apparatus of FIG. 1, in which the apparatus is viewed from the opposite side to FIG. 1.
Figure 2:
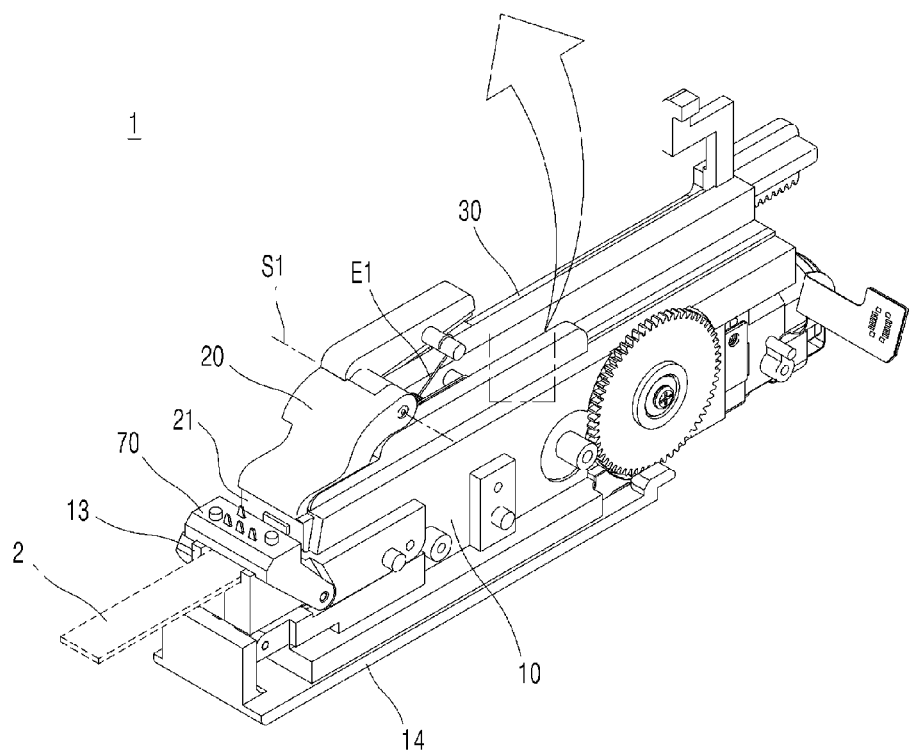
Figure 3:
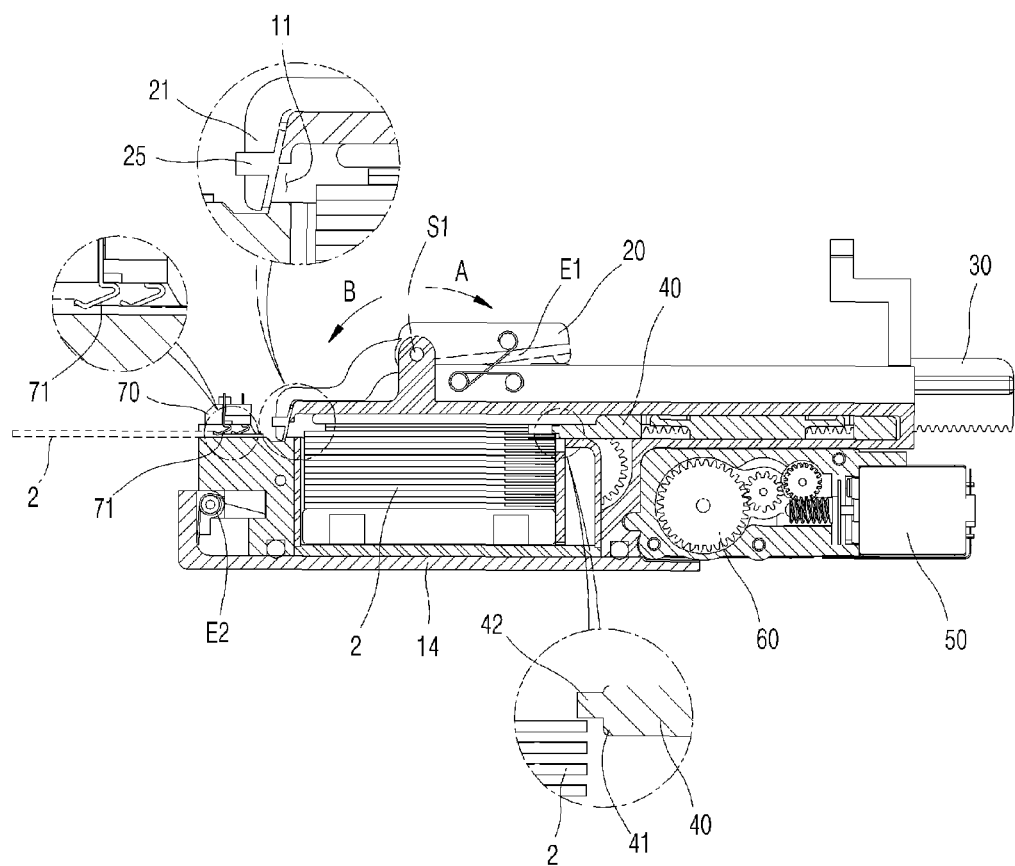
FIG. 3 is a sectional view of the biosensor strip dispensing apparatus illustrated in FIG. 2.
Figure 4:
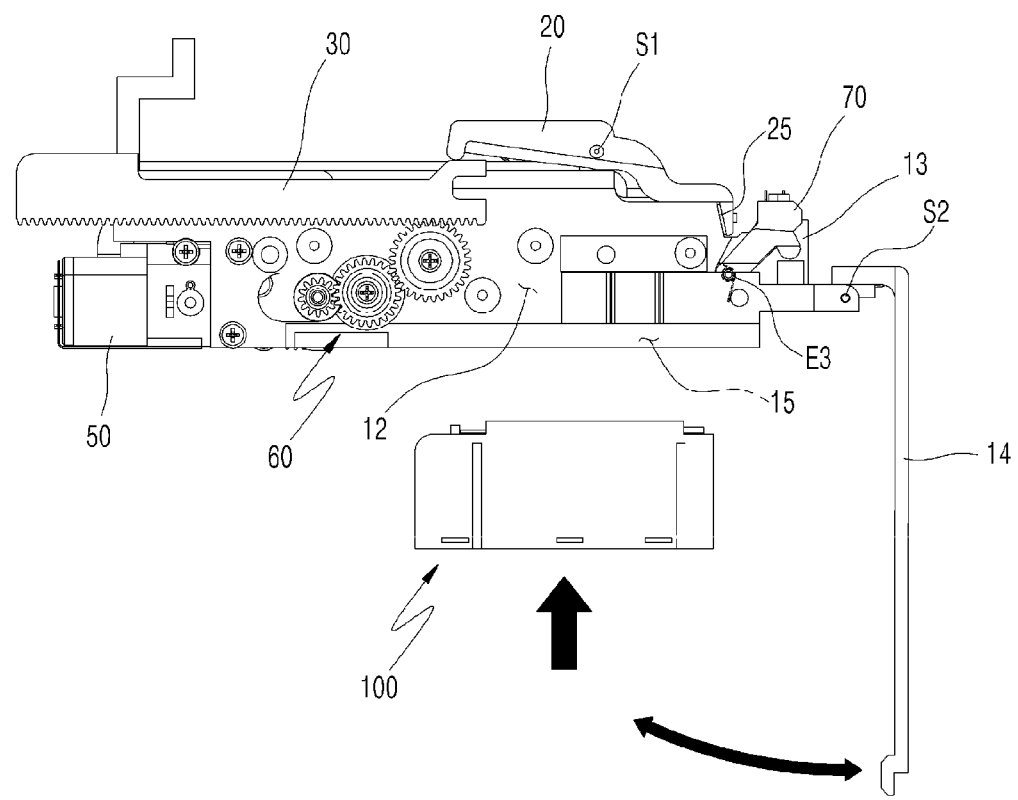
FIG. 4 is a side view illustrating a state in which a door is opened in the biosensor strip dispensing apparatus illustrated in FIG. 1.
Figure 5:
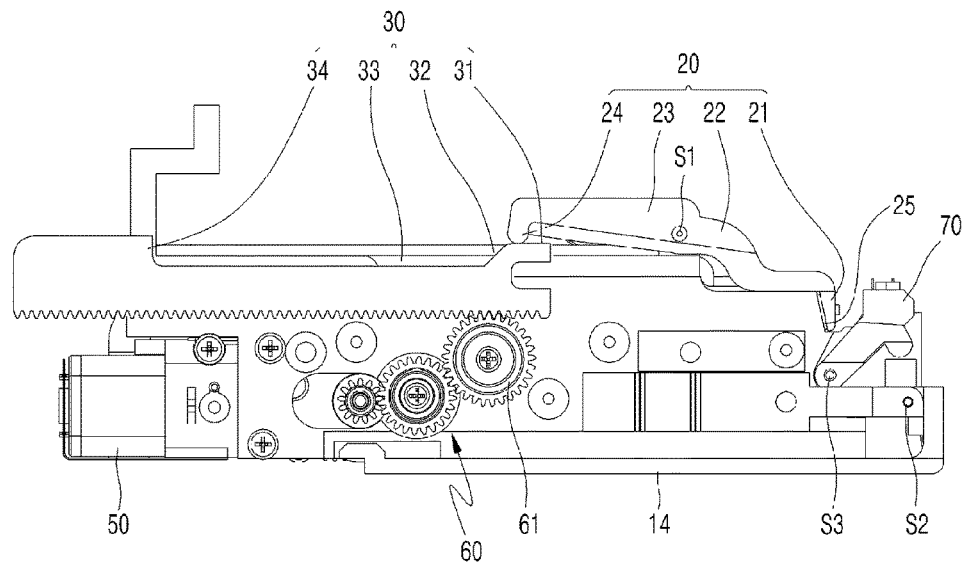
FIG. 5 is a side view of the biosensor strip dispensing apparatus illustrated in FIG. 1.
Figure 6:
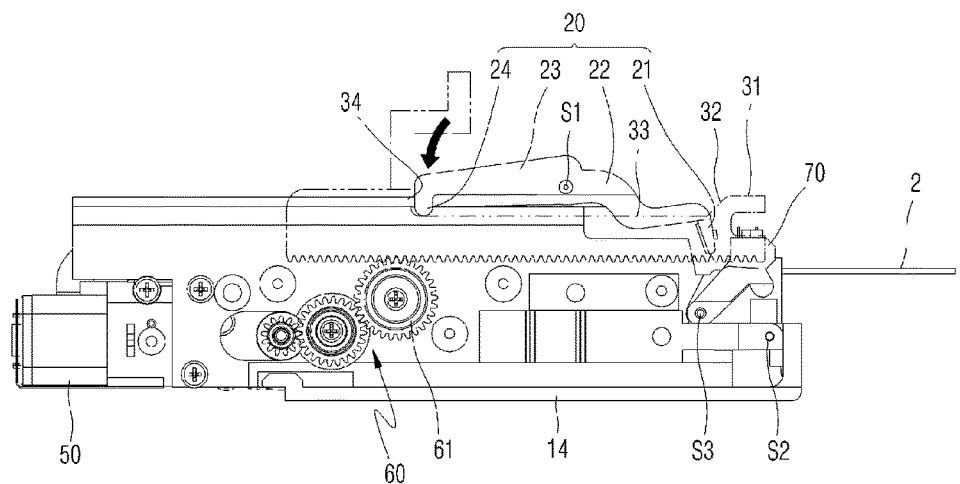
FIG. 6 is a side view illustrating a state in which a strip is dispensed from the biosensor strip dispensing apparatus illustrated in FIG. 5.
Figure 7A:
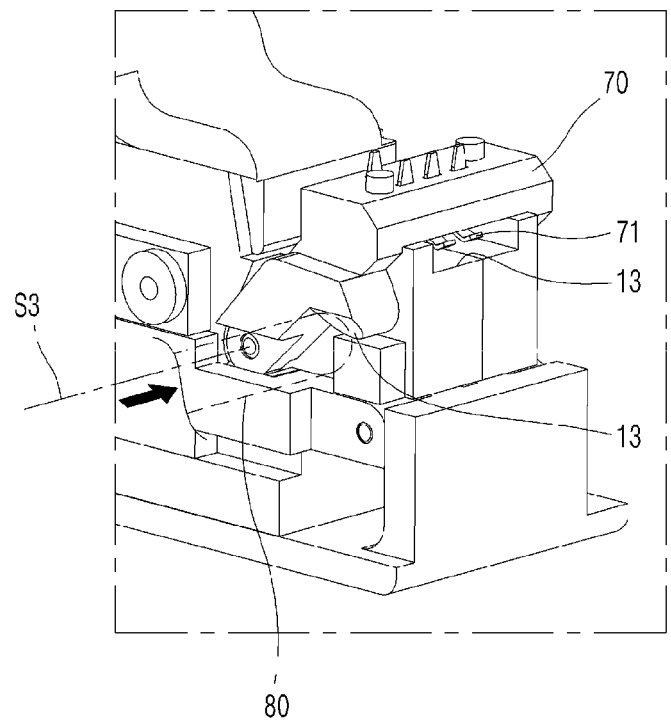
FIG. 7(a) is an enlarged perspective view illustrating a contact terminal section of FIG. 5.
Figure 7B:
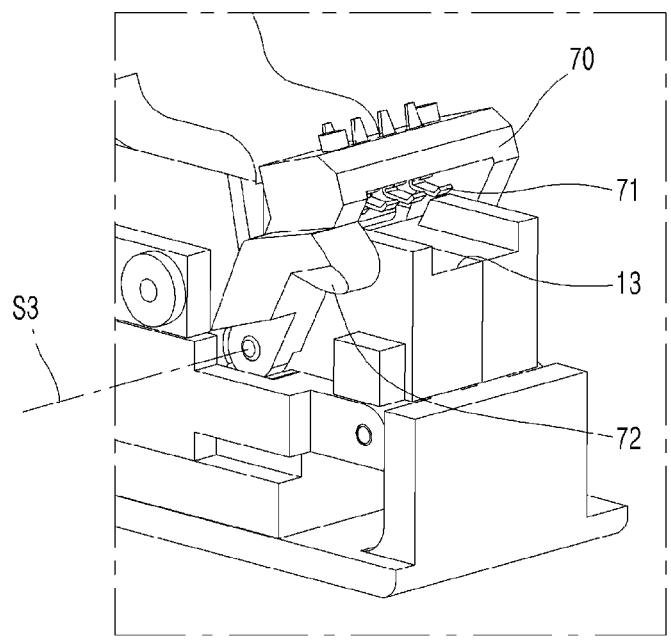
FIG. 7(b) is an enlarged perspective view illustrating the contact terminal section of FIG. 6.

FIG. 1 is a perspective illustrating a biosensor strip dispensing apparatus 1 according to an embodiment of the present disclosure. FIG. 2 is a perspective view illustrating the biosensor strip dispensing apparatus 1 of FIG. 1, in which the apparatus 1 is viewed from the opposite side to FIG. 1. FIG. 3 is a sectional view of the biosensor strip dispensing apparatus 1 illustrated in FIG. 2. FIG. 4 is a side view illustrating a state in which a door 14 is opened in the biosensor strip dispensing apparatus 1 illustrated in FIG. 1. FIG. 5 is a side view of the biosensor strip dispensing apparatus 1 illustrated in FIG. 1. FIG. 6 is a side view illustrating a state in which a strip 2 is dispensed from the biosensor strip dispensing apparatus 1 illustrated in FIG. 5. FIG. 7(a) is an enlarged perspective view of a contact terminal 70 section illustrated in FIG. 5. FIG. 7(b) is an enlarged perspective view of a contact terminal 70 section illustrated in FIG. 6.

In particular, FIGS. 1 to 3 illustrate an appearance of a strip 2 when the strip 2 is dispensed from the biosensor strip dispensing apparatus 1 by dotted lines. In practice, as illustrated in FIG. 3, the strips 2 are stacked and stored inside the biosensor strip dispensing apparatus 1.

The biosensor strip dispensing apparatus 1 according to the present disclosure includes a body 10, a sealing lever 20, an opening plate 30, and a dispensing plate 40. In addition, the biosensor strip dispensing apparatus 1 may further include a drive motor 50, a gear assembly 60, and a contact terminal 70.

Hereinafter, the biosensor strip dispensing apparatus 1 illustrated in FIG. 1 will be described with reference to the front, rear, upper, and lower sides.

The biosensor strip dispensing apparatus 1 according to the present disclosure is configured to store and dispense strips 2, and to further constitute a part of a blood glucose measuring device.

Here, the blood glucose measuring device is configured to measure blood glucose using the biosensor strip 2. The blood glucose measuring device is configured to convert a biological material amount obtained from a blood into an electrical signal, and to measure blood glucose based on the signal.

The biosensor strip 2 used as a direct blood glucose measuring means may be configured like a conventional biosensor, and the strip 2 may include a substrate 2a, a sensor 2b, and electrodes 2c, and may be formed in the form of a conventional l-shaped strip. The strip 2 preferably has a rectangular shape in a plan view, and is formed to be elongated in the front-and-rear direction.

The substrate 2a is made of an insulating material and is formed in the form of a flat plate.

The sensor 2b is a part that is formed on the substrate 2a to generate an electrical signal by electrochemically reacting with a biological sample (blood), and includes an enzyme for an oxidation-reduction reaction action.

The electrodes 2c are made of a conductive material, and are connected to the sensor 2b to transmit a signal generated by the sensor to the measuring device. In the strip 2, the electrodes 2c are formed at the rear portion, and the portion where the electrodes 2c are formed is made to be thinner than the portion where the sensor 2b is formed.

In the strip 2, the sensor 2b is formed to be elongated in the longitudinal direction. After the blood is applied to the front end, and then the state of the blood is sensed through a contact terminal 70 electrically connected to the electrodes 2c of the rear portion.

In the strip 2, the sensor may be configured to measure blood glucose as well as to detect other functions. For example, the sensor may be configured to measure cholesterol or alcohol.

A plurality of strips 2 are provided and disposed in the biosensor strip dispensing apparatus 1 in a stacked state within a strip cartridge (hereinafter, referred to as a "cartridge 100") and are pushed upward by an elastic means (lifting elastic unit 130), and a strip 2 is pushed forward by the dispensing plate 40 to be dispensed to the outside. A detailed description for the cartridge 100 will be followed.

The body 10 forms a whole body of the biosensor strip dispensing apparatus 1 according to the present disclosure, and is provided with a storage hole 12 in which the cartridge 100 filled with the strips 2 is accommodated. The cartridge 100 is inserted into the storage hole 12 from the lower side of the body 10 in the state where latching steps 114 of the housing 110 of the cartridge 100 face upward, to be stored in the storage hole 12.

It is preferable that the body 10 is made to be able to be sealed from the outside in the state where the strips 2 are stored therein, and an inlet port 15 for introducing a strip 2 and a dispensing port 11 for discharging (dispensing) a strip 2 are formed in the body 10.

That is, except for the inlet port 15 and the outlet port 11, the body 10 is kept in the sealed state, and the inlet port 15 and the dispensing port 11 are also configured to be selectively opened, if necessary. Thus, the strips 2 are prevented from being contaminated or damaged by ambient air or moisture. The sealing of the body 10 also doubles the effect of a dehumidifying agent accommodated in a dehumidifying space 112 of the cartridge 100, which will be described later.

The inlet port 15 is formed to be opened to the lower side of the body 10, and the cartridge 100 is inserted through the inlet port 15.

For the effective shielding of the inlet port 15, the door 14 is coupled to the inlet port 15 to be rotatable around the second rotation shaft S2.

In addition, a second elastic unit E2 configured to elastically support the door 14 in the direction in which the door 14 shuts the inlet port 15 is formed. The second elastic unit E2 may be formed in the form of an elastic body (e.g., an elastic spring). That is, in a state in which a separate external force is not applied, the door 14 is rotated in the direction of shielding the inlet port by the action of the second elastic unit E2.

A packing (not illustrated) may be coupled to the door 14 in order to more effectively seal the inlet port 15. At this time, the packing may be made of an elastic rubber.

The dispensing port 11 is formed in the front portion of the body 10 so as to pass through in the front-rear direction, and the lateral width is larger than the vertical height so as to correspond to the cross-sectional shape of the strip 2.

The body 10 is formed with an abutment 13 at a further front side of the dispensing port 11, and the abutment 13 supports the lower portion of the strip 2 dispensed through the dispensing port 11. The abutment 13 has a "U" shape of which the cross section is opened upward when viewed from the front side so as to prevent the strip 2 from moving left and right.

A sealing lever 20 is coupled to the upper side of the body 10 to be rotatable in the opening direction A and the shielding direction B about the first rotation shaft S1. The sealing lever 20 is divided into a covering piece 21, a front arm 22, a rear arm 23, and an adjustment projection 24.

The covering piece 21 is a means for shielding the dispensing port 11, and thus is formed to have an area that is larger than or at least equal to the dispensing port 11. The covering piece 21 is formed in the form of a rectangular block that forms a flat face along a substantially vertical direction.

A packing 25 may be coupled to the covering piece 21 so as to more effectively seal the dispensing port 11. The packing 25 may be made of an elastic rubber.

The front arm 22 is elongated from the first rotation shaft S1 in the forward direction, and the covering piece 21 is integrally formed at the front end of the front arm 22. The length of the front arm 22 in the front-and-rear direction is longer than (preferably, twice or more) the length of the covering piece 21 in the up-and-down direction. As a result, a sufficient movement of the covering piece 21 can be obtained even at a small rotation angle of the front arm 22.

The rear arm 23 is formed to be elongated in the rearward direction from the first rotation shaft S1, and formed integrally with the front arm 22. The length of the rear arm 23 in the front-and-rear direction is longer than (preferably, twice or more) the length of the adjustment projection 24 in the vertical direction. As a result, a sufficient movement of the adjustment projection 24 can be obtained even at a small angle of rotation of the rear arm 23.

The adjustment projection 24 is bent in a downward direction from the rear end of the rear arm 23, and in particular, the lower end surface of the adjustment projection 24 is formed in a downwardly convexly curved surface.

The first elastic unit E1 is coupled to the sealing lever 20. The first elastic unit E1 is formed in the form of an elastic spring to elastically support the sealing lever 20 in the opening direction A. That is, in the state in which no separate external force acts, the sealing lever 20 is rotated in the opening direction A by the action of the first elastic unit E1, and as a result, the covering piece 21 moves so as to bring the dispensing port 11 into the opened state.

The opening plate 30 is a means for rotating the sealing lever 20 in the opening direction A or the shielding direction B. The biosensor strip dispensing apparatus 1 according to the present disclosure is configured such that the opening plate 30 is slid in the front-and-back direction of the body 10 so that the sealing lever 20 can be easily operated while minimizing the total volume of the apparatus, and the sealing lever 20 can be rotated in cooperation with the sliding of the opening plate 30.

Specifically, the opening plate 30 is divided into a front end portion 31, a central portion 33, an inclined portion 32, and a stop portion 34.

The front end portion 31 forms the most front side of the opening plate 30, and supports the lower end of the adjustment projection 24 in the state in which the covering piece 21 shields the dispensing port 11 (in the state in which the sealing lever 20 is rotated in the shielding direction as much as possible). The upper end surface of the front end portion 31 is formed to be parallel to the horizontal direction.

The central portion 33 is a portion formed on the rear side of the front end portion 31. The height of the upper end surface of the central portion 33 is formed to be lower than that of the front end portion 31 so that the central portion 33 supports the lower end of the adjustment projection 24 in the state in which the covering piece 21 opens the dispensing port 11 (in the state in which the sealing lever 20 is rotated in the opening direction A as much as possible). The upper end surface of the central portion 33 is formed to be parallel to the horizontal direction.

The inclined portion 32 is a portion that connects the front end portion 31 and the central portion 33 to each other. The upper end surface forms an inclined surface of which the height is gradually lowered from the front end portion 31 toward the central portion 33, and the lower end portion of the adjustment projection 24 is supported on the inclined surface. By the formation of the inclined portion 32, the adjustment projection 24 can naturally move between the front end portion 31 and the central portion 33, and eventually the soft rotation of the sealing lever 20 is achieved.

The stop portion 34 is a height increasing portion at the rear end of the central portion 33, and preferably the surface thereof is parallel to the vertical direction. That is, the stop portion 34 is formed to prevent the adjustment projection 24 of the sealing lever 20 from moving to the rear side the stopping portion 34.

Accordingly, in the state in which the opening plate 30 is positioned at the rearmost position, the adjustment projection 24 of the sealing lever 20 is supported at the upper end of the front end 31 of the opening plate 30 so that the dispensing port 11 of the body 10 is maintained in the state of being shielded by the covering piece 21. When the opening plate 30 is gradually moved forward and the adjustment projection 24 of the sealing lever 20 is supported on the inclined portion 32 of the opening plate 30, the dispensing port 11 is gradually opened as the covering piece 21 is move by the action of the first elastic unit E1. When the opening plate 30 is further moved forward, the adjustment projection 24 of the sealing lever 20 is supported on the upper end of the central portion 33 of the opening plate 30, and thus the dispensing port 11 is completely opened.

Even when the opening plate 30 is further moved forward (until the adjustment projection 24 comes into contact with the stop portion 34), the adjustment projection 24 of the sealing lever 20 is supported at the same height as the upper end of the central portion 33 of the opening plate 30 so that the opened state of the dispensing port 11 is maintained.

The dispensing plate 40 is a means for causing the strip 2 (the strip located at the uppermost position) to be dispensed to the front side of the body 10 through the dispensing port 11 while being released from the cartridge 100. The biosensor strip dispensing apparatus 1 according to the present disclosure is configured such that the dispensing plate 40 is slid in the front-and-back direction of the body 10 so that the strip 2 can be easily dispensed while minimizing the total volume of the apparatus, and the strip 2 can be dispensed in cooperation with the sliding of the dispensing plate 40.

The dispensing plate 40 is formed with a pressing portion 41 that presses the rear end of the strip 2 (the strip located at the uppermost position) and a supporting portion 42 that supports the rear upper side of the strip 2 toward the lower side. That is, when the pressing portion 41 presses the rear end of the strip 2, the supporting portion 42 prevents the strip 2 from moving upward, and minimizes a force applied in a direction other than the direction that is parallel to the moving direction of the dispensing plate 40, so that smooth dispensing is performed.

The drive motor 50 may be a conventional electric motor, and converts electrical energy into rotational kinetic energy.

The gear assembly 60 connected to the drive motor 50 is formed in the form of an assembly of a plurality of gears and serves as a reduction gear. The gear assembly 60 transmits a rotational force, which is increased by reducing the rotational speed from the drive motor 50, to the opening plate 30 and the dispensing plate 40. The gear assembly 60 includes a first gear 61 and a second gear 62, which are interlocked with each other to be rotated in the same direction.

The connection between the gear assembly 60 and the opening plate 30 and the dispensing plate 40 may be implemented by engagement as in a structure of a rack and a pinion, and as a result, the linear movements of the opening plate 30 and the dispensing plate 40 are performed.

Specifically, a plurality of teeth are repeatedly formed on the bottom surface of the opening plate 30 along the longitudinal direction, and the first gear 61 rotates in the state of being engaged with the teeth of the opening plate 30.

In addition, a plurality of teeth are repeatedly formed on a side of the dispensing plate 40 along the longitudinal direction, and the second gear 62 rotates in the state of being engaged with the teeth of the dispensing plate 40.

Accordingly, as the drive motor 50 rotates, the opening plate 30 and the dispensing plate 40 are slid forward or rearward.

The contact terminal 70 may be configured to be able to support the strip 2 along with the abutment 13. Particularly, the contact terminal 70 is formed with a terminal 71 electrically connected to the electrodes of the strip 2, and the terminal 71 receives an electrical signal from the strip 2, and transmits the electrical signal to a control unit of the blood glucose measuring device. Here, the control unit of the blood glucose measuring device is configured to be capable of expressing a result value (blood glucose value) based on an electrical signal, and may include a microprocessor.

The terminal 71 of the contact terminal 70 is formed in a leaf spring-like shape so that, when the strip 2 is pressed forward by the dispensing plate 40 to be introduced into the gap between the abutment 13 and the contact terminal 70, the terminal 71 of the contact terminal 70 can press the strip 2 interposed naturally therebetween.

The contact terminal 70 is coupled to the body 10 to be rotatable with reference to the third rotation shaft S3.

The third elastic unit E3 is formed to elastically support the contact terminal 70 in the direction in which the contact terminal 70 supports the strip 2, and the third elastic unit E3 may be formed in the shape of an elastic spring. That is, in a state in which no separate external force acts, the contact terminal 70 is rotated in a direction of supporting the strip 2 by the action of the third elastic unit E3, and is maintained in state of being close to the abutment 13 or being in contact with the abutment 13.

Meanwhile, the contact terminal 70 is provided with a pushing surface formed to be inclined along the third rotation shaft S3, and the biosensor strip dispensing apparatus 1 according to the present disclosure is formed with a release button 80 configured to press the pushing surface.

The release button 80 is configured to move back and forth along a direction parallel to the axial direction of the third rotation shaft S3. Therefore, when the release button 80 moves in the direction toward the pushing surface, the pushing surface is moved by being pushed by the release button 80 so that the contact terminal 70 is rotated.

Such an action of the release button 80 can be used when it is desired to easily separate the strip 2 from the abutment 13 after the measurement of blood glucose is completed.

Figure 8:
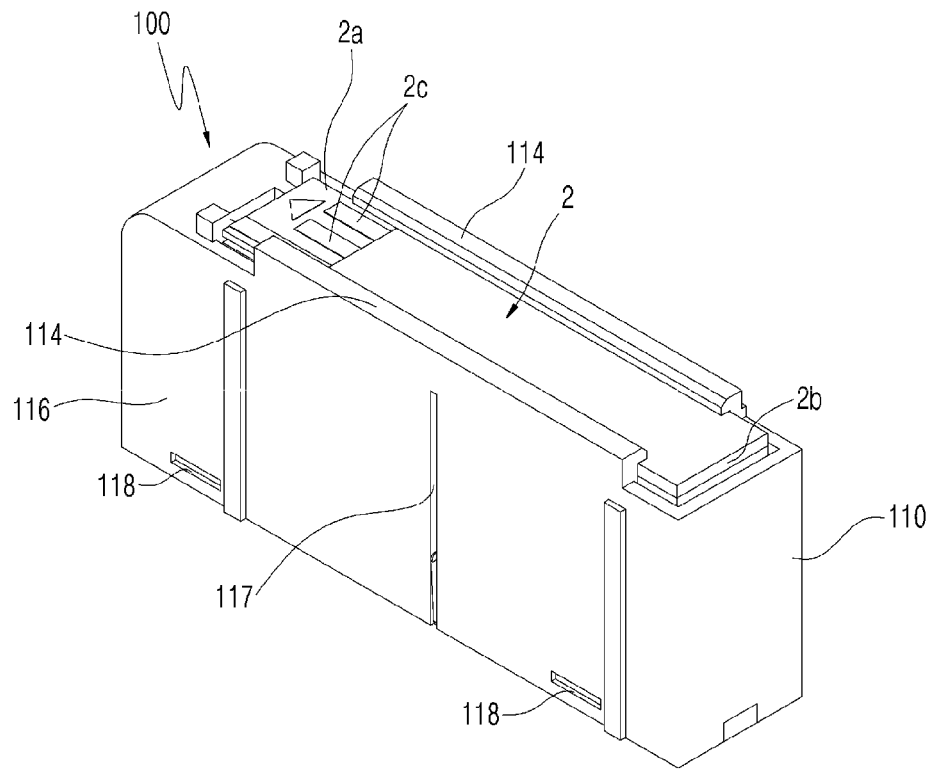
FIG. 8 is a perspective view illustrating a cartridge according to the present disclosure.
Figure 9:
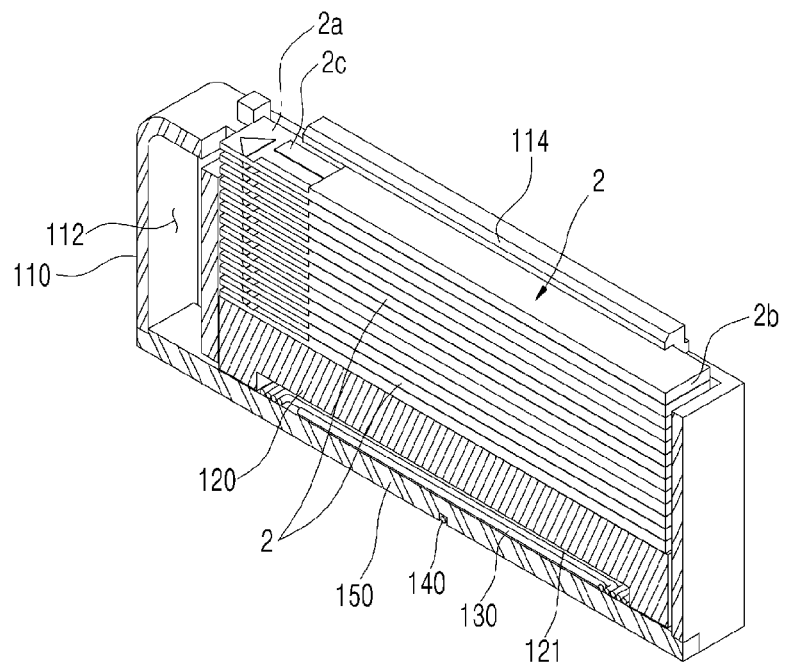
FIG. 9 is a sectional view of the cartridge illustrated in FIG. 8.
Figure 10:
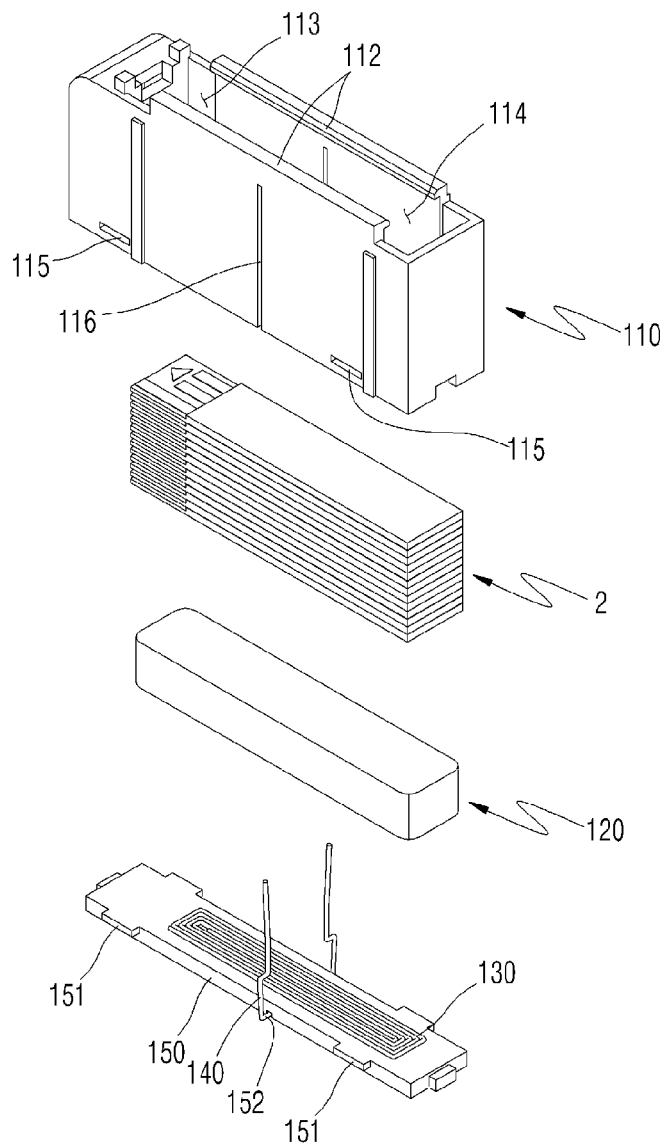
FIG. 10 is an exploded perspective view of the cartridge illustrated in FIG. 8.
Figure 11:
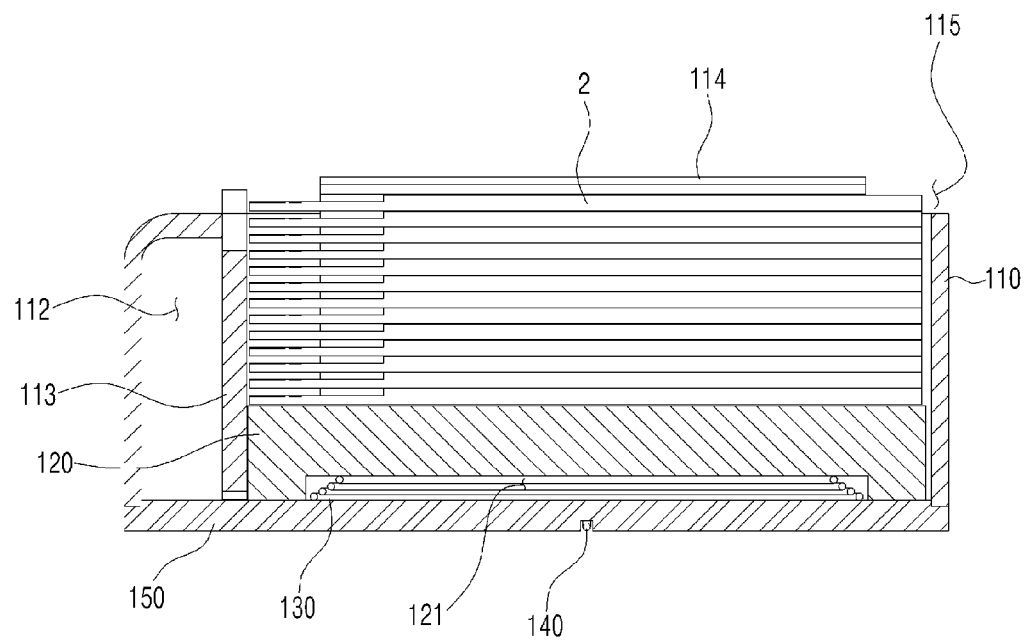
FIG. 11 is a side sectional view of the cartridge illustrated in FIG. 8.
Figure 12:
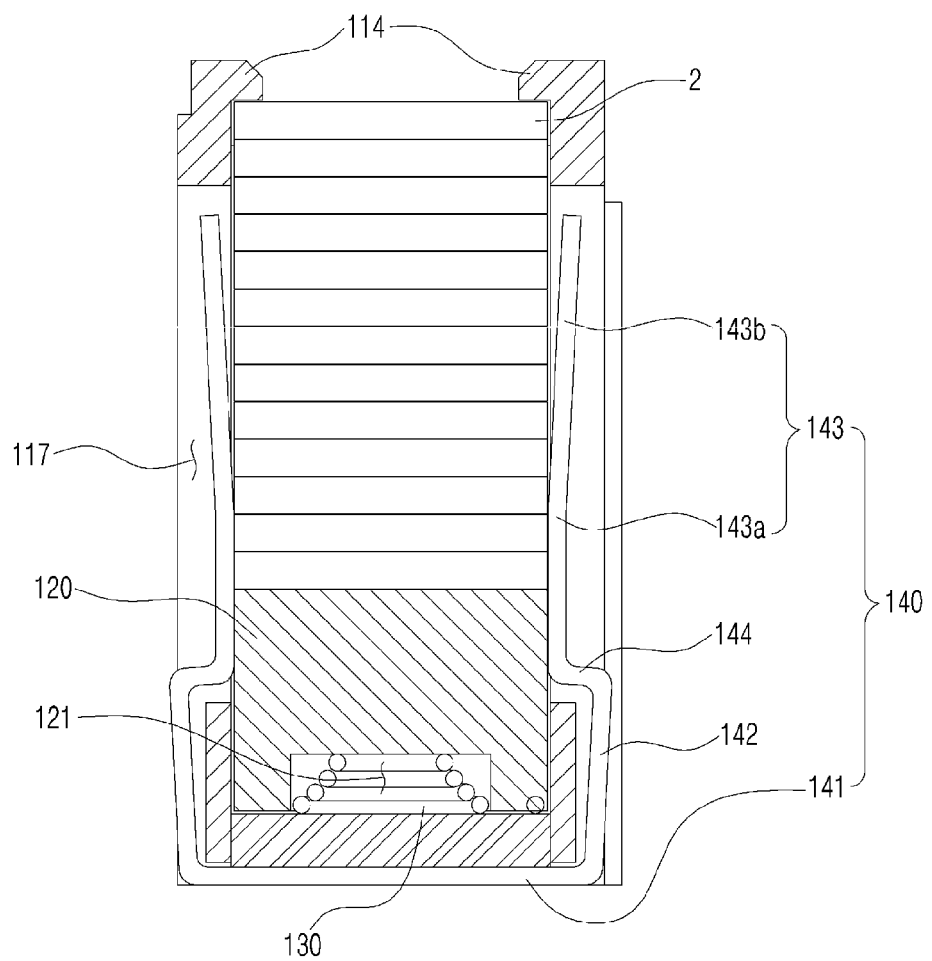
FIG. 12 is a front sectional view of the cartridge shown in FIG. 8.

FIG. 8 is a perspective view illustrating a cartridge 100 according to the present disclosure. FIG. 9 is a sectional view of the cartridge 100 illustrated in FIG. 8. FIG. 10 is an exploded perspective view of the cartridge 100 illustrated in FIG. 8. FIG. 11 is a side sectional view of the cartridge 100 illustrated in FIG. 8. FIG. 12 is a front sectional view of the cartridge 100 shown in FIG. 8. FIG. 13 is a view illustrating a frictional elastic unit 140 separated from FIG. 12. FIG. 14 is a graph representing an elastic force generated by the lifting elastic unit 130 and the frictional elastic unit 140 as the lifting body 120 is moved up within the housing 110.

The cartridge 100 according to the present disclosure includes a housing 110, a lifting body 120, a lifting elastic unit 130, a frictional elastic unit 140, and a base plate 150.

The housing 110 is basically provided with a stacking space 111 as a space in which the strips 2 are stored, and latching steps 114 and a dispensing opening 115 are formed in the upper end of the stacking space 111.

The stacking space 111 is formed to correspond to the shape and size of the strips 2 and may be equal to or slightly larger than the size of the strip 2 in a plan view.

The latching steps 114 are formed at the upper side the stacking space 111 and are symmetrical to each other at the both ends of the upper side of the housing 110. The latching steps 114 are formed in a shape in which the width of the latching steps 114 becomes narrower than the stacking space 111. In particular, the distance between the pair of latching steps 114 is narrower than the width of the strips 2.

Thus, the strips 2, which are pressed upward by the lifting elastic unit 130 and the lifting body 120, are caught by the latching steps 114, and are prevented from being further moved so long as a separate external force is not applied thereto. The pressing portion 41 and the supporting portion 42 of the dispensing plate 40 press the strip 2 forward as passing through the gap between the pair of latching steps 114.

The dispensing opening 115 is formed by removing a portion of the latching steps 114 at the front side of the latching steps 114, and the uppermost strip 2, which is prevented from being upwardly moved by the latching steps 114, is moved forward through the dispensing opening 115 to be released from the cartridge 100.

In addition to the stacking space 111, the housing 110 may be provided with a dehumidifying space 112, which is separated from the stacking space 111 by a partition 113. The stacking space 111 and the dehumidifying space 112 are formed to communicate with each other through the upper end of the partition 113.

The dehumidifying space 112 is filled with a dehumidifying agent, which protects the strips 2 stacked in the stacking space 111 from moisture. In addition, as described above, since the body 10 is normally kept in the closed state, the protection effect of the strip 2 by the dehumidifying agent can be more effectively achieved.

Each of the left and right side walls 116 of the housing 110 is provided with a slit 117 extending in the vertical direction and a frictional elastic unit 140 is inserted into the slits 117. In particular, an elastic storage section 142 and a deformation section 143 of the frictional elastic unit 140 are inserted into the slits 117. The interval of the slits 117 is set to a size corresponding to the diameter of the frictional elastic unit 140 such that unnecessary separation of the frictional elastic unit 140 is prevented while the elastic deformation of the frictional elastic unit 140 is not disturbed.

The lifting body 120 is configured to be slidable in the vertical direction within the housing 110, and is formed in a substantially hexahedral block shape. The lifting body 120 is inserted into the stacking space 111 of the housing 110, and is positioned below the stacked strips 2. It is preferable that the lifting body 120 is formed to minimize the spacing of the lifting body 120 when the lifting body 120 is moved up and down within the stacking space 111. Accordingly, the left-and-right width of the lifting body 120 corresponds to the distance between the side walls 116 of the housing 110

An insertion recess 121 is formed concavely on the bottom surface of the lifting member 120, and the upper portion of the lifting elastic unit 130 is inserted into the insertion recess 121.

The lifting elastic unit 130 may be formed in the shape of an elastic body (e.g., an elastic spring). That is, in the state in which no separate external force acts, the lifting body 120 is urged in the stacking space 111 of the housing 110 in the direction toward the latching steps 114 by the action of the lifting elastic unit 130.

The lifting elastic unit 130 may be formed in the shape of a coil spring (not in the shape of a circular coil spring, but in the shape of a rectangular coil spring as shown in FIG. 10). Although FIG. 10 illustrates the lifting elastic unit 130 in the shape most compressed in the vertical direction, it is of course that as the external force is removed, the height of the lifting elastic unit 130 increases as the elasticity is recovered in the vertical direction.

In the cartridge 100 according to the present disclosure, the elastic force acting by the lifting elastic unit 130 changes depending on the height of the lifting body 120. In particular, when the lifting body 120 is located at a relatively low position, the lifting elastic unit 130 is strongly compressed so that the elastic force (upwardly directed) acting on the lifting body 120 acts strongly. When the lifting body 120 is moved up and located at a relatively high position, the compression of the lifting elastic unit 130 is weakened so that the elastic force (upwardly directed) acting on the lifting body 120 acts is reduced.

That is, unless the action by the frictional elastic unit 140 is taken into consideration as described later, when the lifting body 120 is located at a relatively low position, the frictional force acting between the uppermost strip 2 and the latching steps 114 acts relatively strongly, and when the lifting body 120 is moved up and located at a relatively high position, the frictional force acting between the uppermost strip 2 and the latching steps 114 is reduced.

In other words, even when the frictional elastic unit 140 according to the present disclosure is not provided, the frictional force acting between the strip 2 and the latching steps 114 varies depending on the number of the stacked strips 2. Thus, the force to be exerted by the dispensing plate 40 in sequentially dispensing the strips 2 varies, which eventually acts as a factor of disturbing a smooth operation.

In order to solve this problem, the present disclosure includes the frictional elastic unit 140, and the frictional elastic unit 140 may be formed in the shape of an elastic body (e.g., an elastic spring). The frictional elastic unit 140 is configured to rub against the lifting body 120 so that the force f2 (frictional force) is applied to the lifting body 120 in a direction opposite to the force f1 applied by the lifting elastic unit 130. In particular, the frictional elastic unit 140 is configured such that an acting frictional force varies depending on the position of the lifting body 120. When the lifting body 120 is located at a relatively low position, the amount of deformation is large in order to store a relatively large elastic force, and when the lifting body 120 is located at a relatively high position, the amount of deformation is small in order to store a relatively small elastic force.

The frictional elastic unit 140 may be formed in a bent shape of an elastic body (a metal, a synthetic resin, or a combination thereof). As illustrated in FIGS. 10 to 13, the frictional elastic unit 140 may be formed in the form of a bent wire spring as well as in the form of a bent leaf spring. When the frictional elastic unit 140 is in the form of a leaf spring, each part of the frictional elastic unit forms a flat surface along the front-and-rear direction of the strip cartridge 100.

As illustrated in FIGS. 10 to 13, the frictional elastic unit may be formed of an elastic body that is separate from the housing 110 and the base plate 150. Further, the frictional elastic unit may also be integrally formed with the housing 110 or the base plate 150. That is, the frictional elastic unit may be formed in the form of an elastic body, which is integrally formed with the housing 110 or the base plate 150, but is branched to be elastically deformed.

Hereinafter, descriptions will be made with reference to the frictional elastic unit illustrated in FIGS. 10 to 13.

The frictional elastic unit 140 may be divided into a lower end connection section 141, an elastic storage section 142, a deformation section 143, and an intermediate connection section 144.

The lower end connection section 141 forms the lowermost part of the frictional elastic unit 140 along the horizontal direction.

The elastic storage section 142 includes portions that extend upward from both ends of the lower end connection section 141, respectively. The elastic storage section 142 has a symmetrical structure having a width d1 that is larger than the width of the lifting body 120 in a state in which no external force is applied (see FIG. 13).

The deformation section 143 is located at the upper side of the elastic storage section 142 and includes portions that respectively extend from the left and right portions of the elastic storage sections 142 to form a bilaterally symmetrical structure. In the state where no external force is applied (see FIG. 13), the interval of the portions of the deformation section 143 is at least partially smaller than or equal to the width of the lifting body 120 to be in friction (contact) with the lifting body 120. The upper ends of the deformation section 143 are formed as free ends.

The deformation section 143 is divided into a lower deformation section 143a and an upper deformation section 143b.

The lower deformation section 143a is a lower area of the deformation section 143, which has a width d2 that decreases toward the upper side. It is desirable that the width d2 in the lower deformation section 143a is smaller than the width of the lifting body 120.

The upper deformation section 143b is an upper area of the deformation section 143, which has a width d3 that is formed to be constant or to decrease toward the upper side. Even if the width d3 decreases, it is desirable that the decreasing degree of the width d3 is smaller than that of the width d2 in the lower deformation section 143a. The width d3 in the upper deformation section 143b is smaller than or equal to the width of the lifting body 120.

The intermediate connection section 144 connects the elastic storage section 142 and the deformation section 143, and thus has a bent shape.

In a state in which the cartridge 100 according to the present disclosure is assembled, when the lifting body 120 is sandwiched in the middle of the frictional elastic unit 140, the frictional elastic unit 140 and the lifting body 120 come in contact with each other to generate a frictional force.

When the lifting body 120 comes in contact with the lower deformation section 143a of the frictional elastic unit 140, the deformation section 143 is relatively widened in the lateral direction, and as a result, a relatively strong elastic force is stored in the elastic storage section 142 and the intermediate connection section 144. In addition, the frictional force between the lifting body 120 and the frictional elastic unit 140 also increases due to the storage of the strong elastic force.

When the lifting body 120 moves upward to come in contact with the upper deforming section 143b, the transversely widened degree of the deformation section 143 decreases, and the elastic force generated in the elastic storage section 142 and the intermediate connection section 144 is also somewhat reduced. In addition, the frictional force between the lifting body 120 and the frictional elastic unit 140 also decreases due to the reduction of the elastic force.

As described above, in the cartridge 100 according to the present disclosure, the frictional force f2 acting between the lifting body 120 and the frictional elastic unit 140 changes depending on the height of the lifting body 120. In particular, when the lifting body 120 is located at a relatively low position, the frictional force (directed downward) acting on the lifting body 120 acts strongly, and when the lifting body 120 is located at a relatively high position while the lifting body 120 is lifted, the frictional force (directed downward) acting on the lifting body 120 is reduced.

Consequently, when the stacked strips 2 are sequentially dispensed from the housing 110, the frictional force f2 generated according to the action of the frictional elastic unit 140 is proportional to the elastic force f1 generated due to the action of the lifting elastic unit 130, but the direction of the frictional force f2 is opposite to that of the elastic force f1. Thus, a substantially constant force f3 is applied to the lifting body 120, and a constant frictional force is generated between the uppermost strip 2 and the latching steps 114 (see FIG. 14).

Therefore, when the strips 2 are sequentially dispensed from the cartridge 100, a constant force can be applied to the dispensing plate 40, and a smooth operation can be achieved.

The base plate 150 is formed in the form of a substantially flat plate, and is coupled to the lower end of the housing 110 so as to block the lower side of the stacking space 111 and the dehumidifying space 112.

For the coupling between the base plate 150 and the housing 110, a coupling projection 151 may be formed on one of the base plate 150 and the housing 110, and a coupling recess 118 may be formed on the other of the base plate 150 and the housing 110 such that the coupling projection 151 is inserted into the coupling recess 118.

The lifting elastic unit 130 is placed on the base plate 150, and presses the lifting body 120 upward based on the base plate 150.

A supporting recess 152 is formed concavely on the bottom surface of the base plate 150, and the supporting recess 152 is formed across the right-and-left direction. The size of the supporting recess 152 may be determined to correspond to the diameter of the frictional elastic unit 140.

Although the specific embodiment of the present disclosure has been described above, it is apparent to those skilled in the art that the present disclosure is not limited to the embodiment disclosed herein and various modifications and changes can be made without departing from the spirit and scope of the present disclosure. Therefore, such modifications and changes should not be individually construed from the spirit or point of view of the present disclosure, and it should be understood that modified embodiments belong to the claims of the present disclosure.

INDUSTRIAL UTILITY

The present disclosure provides a compact biosensor strip dispensing apparatus that is excellent in strip protection effect according to the internal sealing of the body while easily dispensing a strip when using the strip. Also, the present disclosure provides a strip cartridge that is capable of reducing a variation in frictional force acting between the strip located at the uppermost position and latching steps, thereby facilitating the dispensing of the strip. In these viewpoints, since the present disclosure overcomes the limits of the existing technologies, there is a good chance that an apparatus to which the present disclosure is applied will be commercially available or will be marketed without being limited to a situation in which the present disclosure uses the related arts. Further, it is practically possible to carry out the present disclosure. Thus, the present disclosure is an industrially applicable disclosure.

* DRAWING LEGEND INSERTION
FIG. 14
FORCE BY LIFTING ELASTIC UNIT (f1)
PRACTICAL PUSHING FORCE (f3=f1−f2)
HEIGHT OF LIFTING BODY
FORCE BY FRICTIONAL ELASTIC UNIT (f2)

The invention claimed is:

1. A biosensor strip dispensing apparatus comprising:
a body configured to accommodate at least one biosensor strip therein, and having a dispensing port formed in a front portion thereof to dispense the biosensor strip through the dispensing port;
a sealing lever provided with a covering piece to shield the dispensing port, the covering piece configured to rotate about a first rotation shaft in (i) an opening direction, in which the covering piece opens the dispensing port, and (ii) a shielding direction that is opposite to the opening direction;
an opening plate connected to or supporting the sealing lever to rotate the sealing lever in the opening direction and the shielding direction while being slid back and forth on the body;
a dispensing plate interlocked with the opening plate to be slid in the same direction as the opening plate, the dispensing plate being configured to push the biosensor strip forward at a rear side of the biosensor strip;
a first elastic unit made of an elastic body and configured to elastically support the sealing lever in the opening direction,
wherein the sealing lever includes:
a front arm extending forward from the first rotation shaft, and connected to the covering piece, which is bent downwardly, at a front end thereof;
a rear arm extending rearwardly from the first rotation shaft; and
an adjustment projection bent downwardly at a rear end of the rear arm, and
wherein the opening plate includes:
a front end portion configured to support a lower end of the adjustment projection in a state where the covering piece shields the dispensing port; and
a central portion extending rearwardly from the front end portion and formed to be lower than the front end portion, the central portion being configured to support the lower end of the adjustment projection in a where the covering piece opens the dispensing port.

2. The biosensor strip dispensing apparatus of claim 1, further comprising a packing, wherein the packing is coupled to the covering piece to seal the dispensing port.

3. The biosensor strip dispensing apparatus of claim 1, wherein the opening plate includes an inclined portion that connects the front end portion and the central portion to each other and supports the lower end of the adjustment projection.

4. The biosensor strip dispensing apparatus of claim 1, wherein multiple biosensor strips are provided and stacked one on another within a cartridge,
the body includes a storage hole formed to accommodate the cartridge, and
the biosensor strip dispensing apparatus further comprises:
a door rotatably coupled to the body to open and close the storage hole; and
a second elastic unit made of an elastic body to elastically support the door in a direction where the door shields the storage hole.

5. The biosensor strip dispensing apparatus of claim 1, further comprising:
a drive motor; and
a gear assembly connecting the drive motor to the opening plate and the dispensing plate.

6. The biosensor strip dispensing apparatus of claim 5, wherein the opening plate is positioned outside the body, the dispensing plate is positioned inside the body, and the gear assembly includes a first gear rotated via a connection to the opening plate and a second gear rotated via a connection to the dispensing plate.

7. The biosensor strip dispensing apparatus of claim 1, further comprising:
an abutment configured to support a lower surface of the biosensor strip when the biosensor strip is dispensed; and a contact terminal configured to support an upper surface of the biosensor strip when the biosensor strip is dispensed, and electrically connected to an electrode of the biosensor strip.

8. The biosensor strip dispensing apparatus of claim 7, wherein the contact terminal is coupled to the body to be rotatable about a third rotation shaft, and the biosensor strip dispensing apparatus further comprises:

an elastic unit made of an elastic body to elastically support the contact terminal in a direction where the contact terminal supports the strip.

9. The biosensor strip dispensing apparatus of claim 8, wherein the contact terminal includes a pushing surface formed to be inclined along the third rotation shaft, and the biosensor strip dispensing apparatus further comprises:

a release button configured to move back and forth with respect to the pushing surface in a direction parallel to the third rotation shaft.

* * * * *